Figure 1:
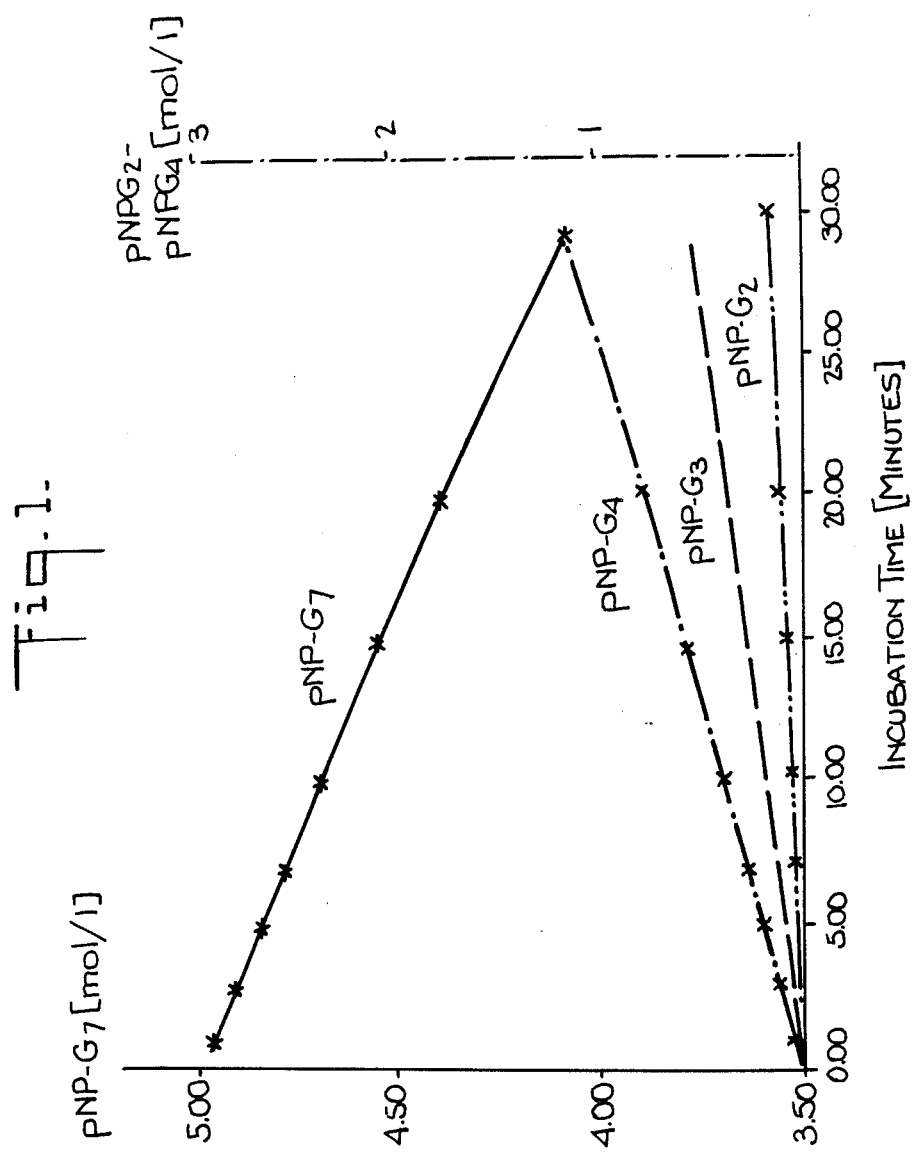

United States Patent [19]

Gerber

[11] Patent Number: 4,945,043

[45] Date of Patent: Jul. 31, 1990

[54] PROCESS AND REAGENT FOR THE DETERMINATION OF α-AMYLASE

[75] Inventor: Martin Gerber, Weilheim-Unterhausen, Fed. Rep. of Germany

[73] Assignee: Boehringer Mannheim GmbH, Mannheim, Fed. Rep. of Germany

[21] Appl. No.: 50,887

[22] Filed: May 15, 1987

[30] Foreign Application Priority Data

Jun. 25, 1986 [DE] Fed. Rep. of Germany ....... 3621271

[51] Int. Cl.$^5$ .................... C12Q 1/40; G01N 33/53
[52] U.S. Cl. .......................... 435/7; 435/22; 435/70.21; 435/172.2; 435/240.2; 435/188; 435/810; 436/537; 436/548
[58] Field of Search ............ 435/22, 188, 7, 14, 435/15, 18, 26, 68, 172.2, 240.2, 810; 436/537, 548

[56] References Cited

U.S. PATENT DOCUMENTS

| 4,446,233 | 5/1984 | Hargreaves et al. | 435/7 |
| 4,493,890 | 1/1985 | Morris | 435/7 |
| 4,544,631 | 10/1985 | Rauscher | 435/14 |
| 4,649,108 | 3/1987 | Blair | 435/22 |

FOREIGN PATENT DOCUMENTS

| 3500526 | 10/1986 | Fed. Rep. of Germany | 435/22 |
| 183098 | 10/1983 | Japan | 435/22 |

OTHER PUBLICATIONS

Tietz, N. (ed), Textbook of Clinical Chemistry, pp. 725–735 (1986).

*Primary Examiner*—Robert J. Warden
*Assistant Examiner*—Carol A. Spiegel
*Attorney, Agent, or Firm*—Felfe & Lynch

[57] ABSTRACT

The present invention provides a process for the determination of α-amylase by cleavage of a substrate in the presence of one or more auxiliary enzymes and measurement of a cleavage product, wherein the reaction is carried out in the presence of monoclonal antibodies against α-amylase.

The present invention also provides a reagent for the determination of α-amylase containing a substrate, one or more auxiliary enzymes and a system for the measurement of a cleavage product, wherein it also contains at least one monoclonal antibody against α-amylase.

31 Claims, 3 Drawing Sheets

PROCESS AND REAGENT FOR THE DETERMINATION OF α-AMYLASE

The present invention is concerned with a process and a reagent for the determination of α-amylase by cleavage of a substrate thereof in the presence of one or more auxiliary enzymes and measurement of a cleavage product.

The determination of α-amylase, as well as of its isoenzymes, is one of the most important methods of clinical chemistry since the results thereof are used for diagnostic purposes, especially for the diagnosis of pancreatic diseases. Consequently, a number of processes has been developed for the determination of α-amylase. For the most part, they depend upon the cleavage of a substrate, frequently in the presence of one or more auxiliary enzymes, and measurement of a cleavage product. Starch derivatised with determinable groups, as well as maltooligosaccharides have, inter alia, achieved technical importance, as is described, for example, in U.S. Pat. Nos. 3,879,263 and 4,000,042 and in Federal Republic of Germany Patent Specification No. 27 41 192. The mentioned maltooligosaccharides can also be modified by groups which can be determined optically, such as are described, for example, in Federal Republic of Germany Patent Specifications Nos. 27 31 421 and 27 55 803, or can have ethylidene protective groups (see European Patent Specification No. 0135758 A1).

A general difficulty of all of these determinations is that the substrates have different points of attack for cleavage by α-amylase and, therefore, different cleavage products arise, in some cases by very complicated mechanisms. An exact calculation of the activities is thereby made very difficult and, in some cases, impairs the exactitude. Thus, for example, in the case of cleavage of the substrate α-(4-nitrophenyl)-maltoheptaose, about 60% maltotetraose results which is only poorly cleaved by the subsequent indicator reaction which is carried out, for example, with α-glucosidase. Analogous difficulties occur in the case of the other maltooligosaccharide substrates and derivatives thereof. The difficulties would be overcome if it were possible to allow the cleavage of the substrates to proceed in such a manner that only maltotriose and maltose or the corresponding derivatives thereof were to be formed.

Furthermore, it would be desirable if it were also possible to increase the rate of cleavage of the substrates.

Therefore, it is an object of the present invention to overcome the above-mentioned difficulties and, in particular, to achieve an improved cleavage pattern of the substrates, as well as an increased cleavage rate.

Thus, according to the present invention, there is provided a process for the determination of α-amylase by cleavage of a substrate in the presence of one or more auxiliary enzymes and measurement of a cleavage product, wherein the reaction is carried out in the presence of monoclonal antibodies against α-amylase.

As substrates for the process according to the present invention, there can be used natural substrates for α-amylase and derivatives thereof, for example starch derivatives and oligo- and polysaccharides. The D-maltooligosaccharides with 2 to 10 glucose units in the molecule which can optionally be substituted by chromophoric groups and/or carry at least one ethylidene protective group, have proved to be especially useful. Those D-maltooligosaccharides which contain 4 to 8 glucose units in the molecule are especially preferred. Suitable chromophoric groups which can easily be determined optically after splitting off include, for example, phenyl, mononitrophenyl, sorbitol and gluconic acid radicals (see Federal Republic of Germany Patent Specification No. 27 55 803). Furthermore, there can also be considered coloured materials or coloured coupling components as substituents, for example fluorescent coloured materials or precursors thereof which can easily be converted in known manner into the actual coloured material. The measurement of these protective groups is well known and does not here require a detailed explanation. Typical examples of substrates which are especially suitable for the process according to the present invention include maltotetraose, maltopentaose, maltohexaose, maltoheptaose and maltooctaose, the mononitrophenyl and dinitrophenyl derivatives thereof, the ethylidene derivatives of the mentioned maltooligosaccharides and the corresponding compounds which contain not only an ethylidene protective group but also a nitrophenyl or dinitrophenyl radical.

The auxiliary enzymes which are to be considered depend upon the nature of the substrate used and serve the purpose, on the one hand, possibly to cleave further the cleavage products formed by the α-amylase or to react further with the formation of end products which can be determined. Thus, in the case of the use of the preferred maltooligosaccharides with 2 to 10 glucose units substituted with nitrophenyl radicals, as auxiliary enzyme there is used α-glucosidase alone in the case of the α-compounds or together with β-glucosidase in the case of β-compounds, for example β-(p-nitrophenyl)-maltoheptasaccharide. In the case of maltoheptaose, cleavage takes place by means of α-amylase with the formation of maltotriose and maltotetraose as the major cleavage products. In turn, α-glucosidase completely cleaves the maltotriose and partially cleaves the maltotetraose to glucose units. The glucose obtained can then be measured by means of one of the conventional processes for the determination of glucose, for example with hexokinase and glucose-6-phosphate dehydrogenase as auxiliary enzymes.

It is also possible to cleave the maltooligosaccharide for example maltoheptaose or maltotetraose, by means of α-amylase to give maltose and then to determine the latter with maltose phosphorylase, β-phosphoglucomutase and glucose-6-phosphate dehydrogenase, also in known manner. The mentioned enzymes are then used as auxiliary enzymes in the process according to the present invention. These and other methods of determination for the cleavage products of α-amylase are known and do not here require further explanation.

As monoclonal antibodies, in the scope of the present invention those are preferably used which are formed by the hybrid cell clones 469A12 (ECACC 86020601) or 472G12 (ECACC 86020602). However, the process according to the present invention can also be carried out with other monoclonal antibodies which are directed against α-amylase. These monoclonal antibodies can be obtained by the processes conventional for this purpose, thus especially by the use of α-amylase as immunogen in an appropriate experimental organism, obtaining and fusing the spleen cells which produce antibodies directed against the immunogen with myeloma cells or other cells bringing about permanent cultivatability and culturing and selecting the so obtained cell clones according to the antibodies formed.

As experimental animals for the immunization, there can be used, for example BALB/c mice and the immunization itself can take place with complete or incomplete Freund's adjuvant or only in physiological saline. After immunization has taken place, the spleen cells of the experimental animals are fused with myeloma cells and allowed to grow in culture dishes or as ascites and sorted.

Whether an antibody against α-amylase is appropriate for the present invention can easily be ascertained by means of a few preliminary experiments. In this case, it only has to be determined whether the effect according to the present invention takes place. However, an especially simple screening process consists in merely ascertaining whether the monoclonal antibody to be assessed binds at all to the enzyme when certain monoclonal antibodies are present which occupy those binding places on the enzyme which do not give any advantageous action in the sense of the present invention. For this purpose, it is preferred to use monoclonal antibodies which are formed by the hybrid cell clones NCACC 84111301, NCACC 84122003, NCACC 85022203 and ECACC 86060601. An α-amylase complexed with these antibodies only binds with those antibodies which exert the action according to the present invention.

By means of the addition according to the present invention of monoclonal antibodies against α-amylase, there is, surprisingly, achieved in some cases a considerable increase of the enzyme activity, namely, for both isoenzymes of α-amylase. This increase of an isoenzyme is, surprisingly, also maintained when the other isoenzyme is excluded by the addition of monoclonal antibodies which specifically inhibit this isoenzyme. In the following Table 1, there is indicated the influence of various monoclonal antibodies from ascites on the activities of human salivary (h-SA) α-amylase and pancreatic (h-PA) α-amylase in the case of different substrates. Furthermore, by means of the method according to the present invention, the cleavage pattern of the substrates is also advantageously changed in such a manner that a greater proportion of directly determinable cleavage products is formed than without the addition of the monoclonal antibodies. This is indicated in the following Table 2 in which, for two different substrates, in each case there is shown the activity and composition of the cleavage products without and with the monoclonal antibodies used according to the present invention.

Figure 2:
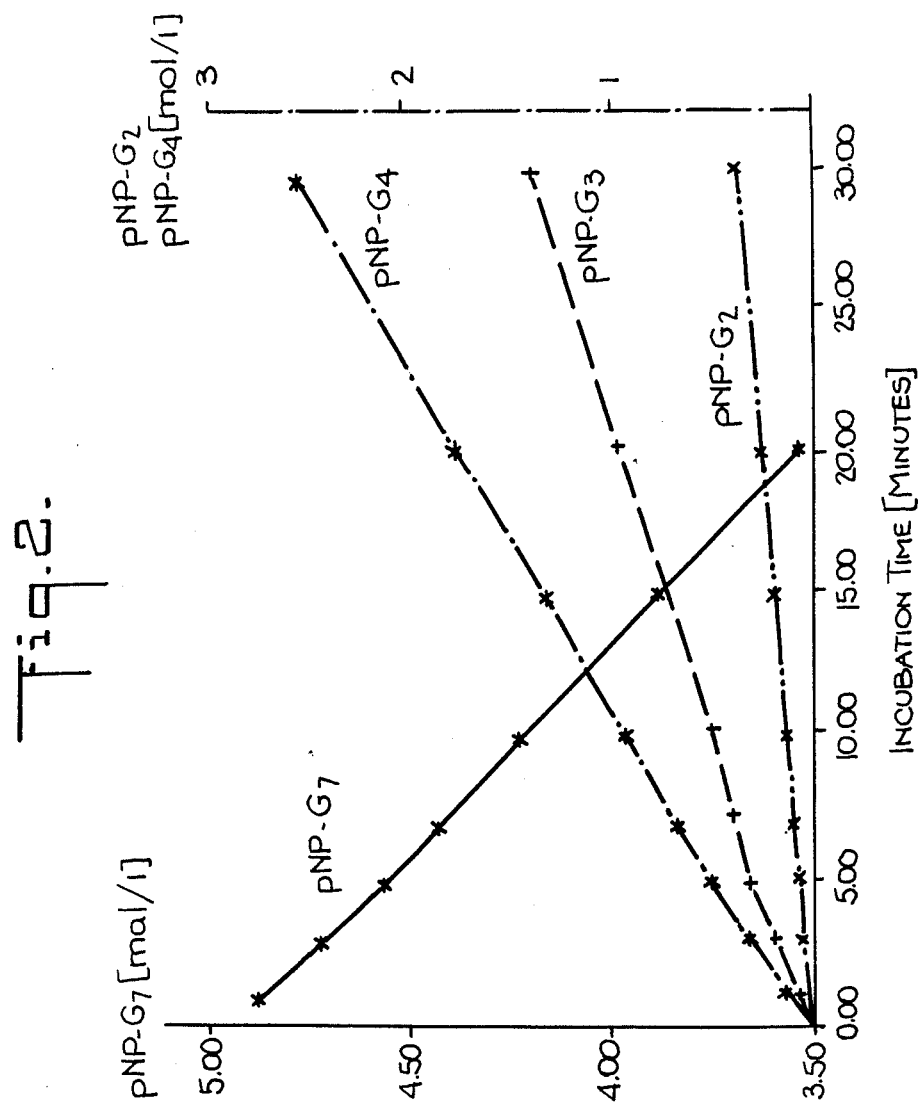
Figure 3:
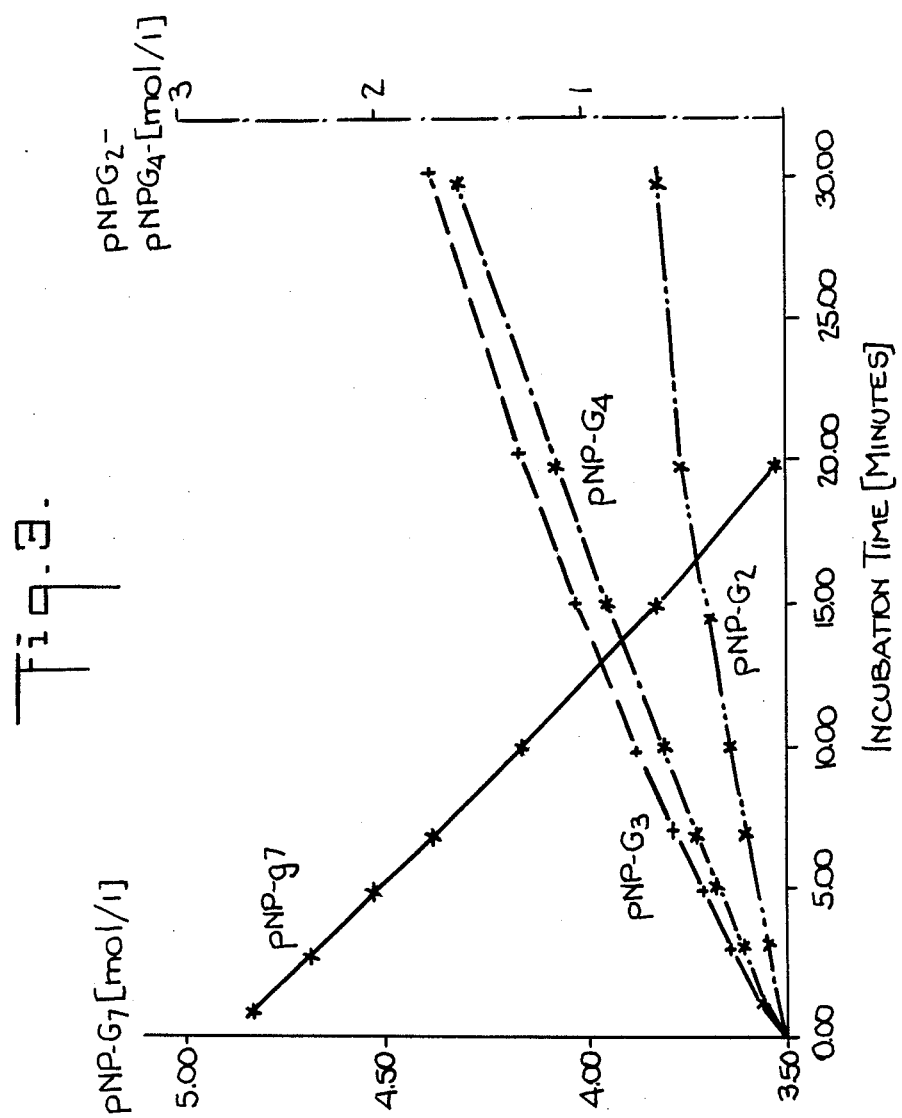

The cleavage patterns determined for the first three experiments according to Table 2 are shown graphically in FIGS. 1, 2 and 3 of the accompanying drawings and clearly demonstrate the surprising effect achieved by means of the present invention.

TABLE 1

Influence of various monoclonal antibodies from ascites on the activities of human salivary (h-SA) and pancreatic (h-PA) α-amylase in combination with different substrates (cf. Example 1)

| MABs of the hybrid cell clones | $G_5$-pNP[1] h-SA[5] | h-PA[6] | $G_6$-pNP[2] h-SA | h-PA | $G_7$-pNP[3] h-SA | h-PA | ethG$_7$-pNP[4] h-SA | h-PA |
|---|---|---|---|---|---|---|---|---|
| without | 100% | 100% | 100% | 100% | 100% | 100% | 100% | 100% |
| ECACC 86020602 | 115% | 116% | 108% | 119% | 121% | 122% | 131% | 128% |
| ECACC 86020601 | 118% | 154% | 142% | 164% | 175% | 188% | 148% | 156% |
| ECACC 86020602+ | — | 123% | 13% | 130% | 19% | 121% | 16% | 128% |
| ECACC 86020601+ | 4% | 158% | 4% | 171% | 4% | 178% | 3% | 148% |
| + | 4% | 99% | 2% | 88% | 3% | 97% | 3% | 100% |
| NCACC 84122003 | 7% | 99% | 10% | 95% | 8% | 100% | 8% | 99% |

[1] p-nitrophenyl-maltopentaose
[2] p-nitrophenyl-maltohexaose
[3] p-nitrophenyl-maltoheptaose
[4] p-nitrophenyl-ethylidenemaltoheptaose
[5] human salivary α-amylase
[6] human pancreatic α-amylase
+ = (+) NCACC 84 122 003 + NCACC 84 111 301

TABLE 2

Influence of the monoclonal antibodies ECACC 86020601 and 86020602 on human pancreatic α-amylase, on the cleavage pattern as well as on the rate of reaction of the substrates $G_7$-pNP and ethG$_7$-pNP (cf. Example 2)

| substrate | MAB from the hybrid cell clone ECACC No. | reaction velocity (i.e. decrease of substrate) ΔmMol 1 min | % act. referred to the activity without MAB | proportion of various products $G_4$-pNP[3] | $G_3$-pNP[4] | $G_2$-pNP[5] | FIG. No. |
|---|---|---|---|---|---|---|---|
| $G_7$-pNP[1] | — | 3.0 · 10$^{-2}$ | 100% | 63% | 29% | 8% | 1 |
| $G_7$-pNP | 86020602 | 7.4 · 10$^{-2}$ | 243% | 60% | 31% | 9% | 2 |
| $G_7$-pNP | 86020601 | 7.5 · 10$^{-2}$ | 247% | 41% | 43% | 16% | 3 |
| ethG$_7$-pNP[2] | — | 1.4 · 10$^{-2}$ | 100% | 22% | 41% | 37% | |
| ethG$_7$-pNP | 86020602 | 3.6 · 10$^{-2}$ | 257% | 19% | 44% | 37% | |
| ethG$_7$-pNP | 86020601 | 4.3 · 10$^{-2}$ | 307% | 10% | 40% | 50% | |

[1] p-nitrophenyl-maltoheptaose
[2] p-nitrophenyl-ethyldenemaltoheptaose
[3] p-nitrophenyl-maltotetraose
[4] p-nitrophenyl-maltotriose
[5] p-nitrophenyl-maltobiose The present invention also provides a reagent for determining α-amylase which contains a substrate, one or more auxiliary enzymes and a system for measuring a cleavage product, wherein it also contains at least one monoclonal antibody against α-amylase. These components may be, e.g., in the form of a kit as separate samples of each.

As monoclonal antibodies, this reagent preferably contains the monoclonal antibodies formed by the hybrid cell clones 469A12 (ECACC 86020601) and/or 472G12 (ECACC 86020602).

With regard to the appropriate substrates and auxiliary enzymes, the statements made above with regard to the process apply correspondingly. If the reagent is used for determining one of the isoenzymes of α-amylase, then it additionally contains one or more monoclonal antibodies against the other α-amylase isoenzyme in question. For a reagent for the determination of pancreatic α-amylase, it is preferred to add monoclonal antibodies against salivary α-amylase which are formed by the hybrid cell clone NCACC 84122003 and possibly to add monoclonal antibodies which are formed by the hybrid cell clone NCACC 84111301.

By means of the present invention, the activity of α-amylase, depending upon the substrate, is increased by 30 to more than 100% and, at the same time, the cleavage pattern is improved. In this way, there is provided a more sensitive test not only for total α-amylase but also for the isoenzymes, especially pancreatic amylase.

The following Examples are given for the purpose of illustrating the present invention:

EXAMPLE 1

I: Immunization of mice by means of human salivary α-amylase

Materials

BALB/c mice, female, about 6 to 8 weeks old
human salivary α-amylase (Sigma, Order No. A 0521)
Freund's adjuvant, complete (Sigma, No. F 5881)
Freund's adjuvant, incomplete (Sigma, Order No. F 5506)
physiological saline (Sigma, No. P 8033)

Reagents

A: 300 μg./ml. salivary α-amylase in complete Freund's adjuvant
B: 150 μg./ml. salivary α-amylase in incomplete Freund's adjuvant
C: 150 μg./ml. salivary α-amylase in physiological saline Carrying out BALB/c mice are immunized with 300 μl. of reagent A. In an about 8 week period, further immunization is carried out 3 or 4 times with, in each case, 300 μl. of reagent B. 4 days before fusion, there is carried out the last immunization intravenously with 300 μl. of reagent C.

II: Fusion of the spleen cells

The fusion of the spleen cells with Ag 8.653 (ATCC CRL 1580) or Sp2/O (ATCC CRL 1581) myeloma cells is carried out according to the standard process described in J. of Immun. Meth., 39, 285–308. The fusion ratio of spleen to myeloma cells is 5:1. The fusion products are seeded out on to 20 24-hole culture dishes (Costar) and fed with $5 \times 10^4$ peritoneal exudate cells per culture cup. Positive primary cultures (see C) are, 3 to 4 weeks after fusion, cloned with the help of a fluorescence-activated cell sorter. The cells are placed individually in a 96-Costar plate and fed with $2 \times 10^4$ peritoneal exudate cells. As culture medium, there is used a commercially available RPMI-1640 medium with 10% fetal bovine serum (described in J.A.M.A., 199, 519/1957).

III: Screening system for α-amylase-activated antibodies

In order to detect the concentration of amylase-activating antibodies in the serum of immunized mice or in the culture supernatant of the hybrid cells or in ascites, there is used an amylase activation test as screening assay. For this purpose, in 96-ELISA plates (Nunc, Denmark) there are placed 50 μl. pancreatic or salivary α-amylase (about 400 U/l.) in buffer (50 mmole/l. tris-HCl; 1% bovine serum albumin and 0.1 mole/liter sodium chloride; (pH 7.5) and pre-incubated for 20 minutes at ambient temperature with 50 μl. of the solution to be tested, for example culture supernatant, serum in various dilutions (with physiological saline) or ascites in various dilutions (with physiological saline).

Thereafter, the enzyme reaction is started with 50 μl. amylase substrate (4-nitrophenylmaltoheptaoside with α-glucosidase; Boehringer Mannheim GmbH, catalogue order No. 568589). After 20 to 60 minutes at ambient temperature, the extinctions are determined at 405 nm in a photometer (ELISA Reader, Kontron, Switzerland) (value I).

The following control is determined at the same time: fresh culture medium (value II). The activation is expressed as a percentage, referred to value II:

$$\frac{value\ I}{value\ II} \times 100\% = \%\ activation$$

The following results are achieved with the test system:

| culture supernatant of the clone | ECACC + | ECACC ++ | NCACC 84122003 | NCACC 84111301 | control culture medium |
|---|---|---|---|---|---|
| % activation of salivary amylase | 120% | 175% | 9% | 98% | 100% |
| % activation of pancreatic amylase | 122% | 188% | 102% | 97% | 100% |

+ = 86020602
++ = 86020601

From about 2% of the primary cultures, there can be found activating monoclonal antibodies.

IV: Production of ascites $1-2 \times 10^6$ hybrid cells (of the cell line 86020601 or 86020602) are injected intraperitoneally into BALB/c mice (about 3 months old) which had been pre-treated once or twice with, in each case, 0.5 ml. "Pristane Oil" (Sigma, Catalogue Order No. T 7640). After about 15 to 20 days, per mouse there are removed 3 to 5 ml. of ascites which contains about 10 mg./ml. IgG.

EXAMPLE 2

Influence of the activating MABs ECACC 86020602 and ECACC 86020601 on the activity of human salivary α-amylase and of human pancreatic α-amylase, also in combination with MABs NCACC 84122003 and NCACC 84111301.

Substances

EnzAmyl K-test for α-amylase (Gödecke AG, Berlin, catalogue order No. 847 903); substrate=maltotetraose Phadebas test for α-amylase (Pharmacia, Freiburg, catalogue order No. 51-5221-00/1); substrate=blue colored, high molecular weight starch 4-nitrophenyl-α-D-maltotetraoside, $G_4$-pNP (Boehringer Mannheim GmbH, catalogue order No. 720 518)

4-nitrophenyl-α-D-maltopentaoside, $G_5$-pNP (Boehringer Mannheim GmbH, catalogue order No. 720 496)

4-nitrophenyl-α-D-maltohexaoside, $G_6$-pNP (Boehringer Mannheim GmbH, catalogue order No. 720 488)

4-nitrophenyl-α-D-maltoheptaoside, $G_7$-pNP (Boehringer Mannheim GmbH, catalogue order No. 720 470)

4,6-ethylidene-4-nitrophenyl-α-D-maltoheptaoside, ethG$_7$-pNP (prepared according to Federal Republic of Germany Patent Specification No. 33 28 616)

ascites from mice of the cell lines ECACC 86020602, ECACC 86020601, NCACC 84122003, NCACC 84111301 (produced analogously to Example 1, IV)

human salivary α-amylase (Sigma, catalogue order No. A 0521)

human pancreatic α-amylase (prepared according to D. J. Stiefel and P. J. Keller, Biochim, Biophys. Acta, 302, 345 361/1973)

bovine serum albumin (BSA) (Boehringer Mannheim GmbH, catalogue order No. 238 031)

α-glucosidase (Boehringer Mannheim GmbH, catalogue order No. 750 590).

Reagents

A: PBS: 100 mM phosphate buffer, 150 mM sodium chloride, pH=7.1
B: PBS/BSA: PBS with 6% bovine serum albumin
C: h-SA solution: human salivary α-amylase in PBS/BSA, 500 U/l. (determined at 25° C. with commercially available reagent α-amylase PNP, Automat package, Boehringer Mannheim GmbH, catalogue order No. 568 589)
D: h-PA solution: human pancreatic α-amylase in PBS/BSA, 500 U/l. (determined like h-SA solution)
E: amylase reagent (with, in each case, a pNP substrate):
  100 mMole/liter hepes buffer (pH 7.1)
  50 mMole/liter sodium chloride
  5 mMole/liter pNP substrate (in each case one substrate
  30 U/liter α-glucosidase
F: ascites dilutions: the various ascites are, in each case, diluted 1:50 with PBS/BSA.

Carrying out

1. Preparation of the amylase with MABs from ascites

100 μl. amylase (h-SA or h-PA) are mixed with 10 μl. of the various ascites dilutions (one or more) and made up to 200 μl. with PBS/BSA. As control, there is used amylase which is only made up with PBS/BSA. The mixtures are incubated for 5 minutes at ambient temperature.

2. Determination of the amylase activity with the substrate $G_4$

The determination of the amylase activity of the amylase-MAB mixtures or of the corresponding controls takes place with the Godecke EnzAmyl K test at 25° C., precisely according to instructions.

3. Determination of the amylase activity with high molecular weight substrate

The determination of the amylase activity of the amylase-MAB mixtures or of the corresponding controls takes place with the Phadebas test of the firm Pharmacia, precisely according to instructions.

4. Determination of the amylase activity with the pNP substrate 1 ml. of the amylase reagent E is warmed to 25° C. in a semimicrocuvette. 50 μl. amounts of the amylase-MAB mixtures or controls are added thereto and well mixed. There takes place the determination of the extinction change ΔE/min. between the 3rd and 7th minute after the amylase-MAB addition at 405 nm.

Calculation

1. $G_4$ substrate and high molecular weight substrate

The amylase activities of the amylase-MAB mixtures obtained as units per liter (U/l.) are referred to the corresponding amylase activities of the controls (without MABs) in the same substrate and given as percentages.

2. pNP substrates

The amylase activities of the amylase-MAB mixtures obtained as ΔE/min. are referred to the corresponding amylase activities of the controls (without MABs) with the same pNP substrate and given as percentages.

Results

The influences of the monoclonal antibodies on the activities of the salivary and pancreatic amylase are summarized in Table 1 in the case of various substrates as percentages of the activity referred to the activity without MABs.

EXAMPLE 3

Determination of the cleavage pattern of $G_7$-pNP and ethG$_7$-pNP by human pancreatic α-amylase with and without monoclonal antibodies ECACC 86020601 and ECACC 86020602, as well as the reaction rate of the cleavage.

Substances 4,6-ethylidene-4-nitrophenyl-α-D-maltoheptaoside, ethG$_7$-pNP (prepared according to Federal Republic of Germany Patent Specification No. 33 28 616)

4-nitrophenyl-α-D-maltoheptaoside, $G_7$-pNP (Boehringer Mannheim GmbH, catalogue order No. 720 470)

ascites of the cell line ECACC 86020601
ascites of the cell line ECACC 86020602
human pancreatic α-amylase (prepared according to D. J. Stiefel and P. J. Keller, Biochim, Biophys. Acta, 302, 345–361/1975)
bovine serum albumin (BSA) (Boehringer Mannheim GmbH, catalogue order No. 238 031).

Reagents

A: 150 mM Hepes buffer, 50 mM sodium chloride, 1 mg./ml. sodium azide (pH 7.1)

B: 100 mM phosphate buffer, 150 mM sodium chloride, 6% BSA (pH 7.1)
C: human pancreatic α-amylase in buffer B, 756 U/ml. (determined at 25° C. with commercially available reagent α-amylase pNP, automat package, Boehringer Mannheim GmbH, catalogue order No. 568 589)
D: monoclonal antibody ECACC 86020601: ascites diluted 1:50 with B
E: monoclonal antibody ECACC 86020602: ascites diluted 1:50 with B
F: 20 parts acetonitrile mixed with 2 parts of 1 mole/liter phosphoric acid
G: 1 part 25 mMole/liter dipotassium monohydrogen phosphate (pH 7.1) mixed with 1 part acetonitrile
H: 5 mM ethG$_7$-pNP in A
I: 5 mM G$_7$-pNP in A Carrying out 1. Mixing of amylase and MABs.

20 μl. MAB solution D or E or buffer B are mixed with 200 μl. pancreatic amylase C and incubated for 5 minutes at ambient temperature.

2. Reaction of amylase/MAB with substrate.

2 ml. of substrate solution (H or I) are taken and warmed to 25° C. The warmed subtrate solution is started with 200 μl. of the various amylase/MAB (buffer) mixtures from 1. After precisely 1, 3, 5, 7, 10, 20 and 30 minutes, 200 μl. aliquots of the started substrate solution are removed and added to 130 μl. of stop reagent F. The stopped aliquots are diluted with 1 ml. of the solution, G and stored at −20° C.

3. Determination of the substrate and of the cleavage fragments of the substrate by HPLC.

The stopped, diluted aliquots from 2 are thawed out. The content of G$_7$-pNP and of ethG$_7$-pNP is determined, whereby pNP and G$_1$-pNP to G$_6$-pNP (the individual aliquots) are determined by HPLC precisely as described by E.-O. Hagele et al. (Clin. Chem., 28 (11), 2201–2205/1982).

Results

In the course of the reaction of the amylase with the substrate, the content of substrate decreases. Table 2 shows the mmole/(1 min.) for the two substrates without MABs, as well as with the MABs ECACC 86020601 and ECACC 86020602. Furthermore, the activity values of the pancreatic amylase, standardised with MABs, are referred to the activities without MABs. In the case of the reactions, no free pNP, no G$_1$-pNP, as well as no G$_5$-pNP and G$_6$-pNP result. The percentage values of the other fragments are also summarized in Table 2.

FIGS. 1 to 3 of the accompanying drawings show the rate of decrease of the substrate, as well as the increase of the products in the case of the pancreatic amylase reaction for G$_7$-pNP as substrate with and without MAB.

EXAMPLE 4

Activation of human α-amylase by the MABs ECACC 86020601 and ECACC 86020602 in the case of the substrate maltoheptaose.

Substances

Monotest α-amylase UV (Boehringer Mannheim GmbH, catalogue order No. 240 001)
ascites from mice of the cell line ECACC 86020602 or ECACC 86020601 (according to Example 1)
human salivary α-amylase (Sigma, catalogue order No. A 0521)
human pancreatic α-amylase (prepared according to D. J. Stiefel and P. J. Keller, Biochem. Biophys. Acta, 302, 345–361/1973)
bovine serum albumin, BSA (Boehringer Mannheim GmbH, catalogue order No. 238 031)

Reagents

A: PBS/BSA: 100 mole/liter phosphate buffer, 150 mole/liter sodium chloride, 6% BSA (pH 7.1)
B: h-SA solution: human salivary α-amylase in PBS/BSA 500 U/liter (determined at 25° C. with commercially available reagent α-amylase PNP, automat package, Boehringer Mannheim GmbH, catalogue order No. 568 589)
C: h-PA solution: human pancreatic α-amylase in PBS/BSA, 500 U/liter (determined as h-SA solution)
D: ascites dilution of the MAB ECACC 86020601: ascites diluted 1+50 with PBS/BSA
E: ascites dilution of the MAB ECACC 86020602: ascites diluted 1+50 with PBS/BSA.

Carrying out

α-Amylase and MABs or buffer are mixed according to the following scheme:

TABLE 3

| | Mixtures of Samples With Various Reagents | | | | |
| | Solution | | | | |
| sample | A | B | C | D | E |
|---|---|---|---|---|---|
| I | 10 μl. | 100 μl. | — | — | — |
| II | 10 μl. | — | 100 μl. | — | — |
| III | — | 100 μl. | — | 10 μl. | — |
| IV | — | 100 μl. | — | — | 10 μl. |
| V | — | — | 100 μl. | 10 μl. | — |
| VI | — | — | 100 μl. | — | 10 μl. |

The samples I–VI are incubated for 10 minutes at ambient temperature.

The activity of samples I–VI are determined at 25° C. with the Monotest-α-amylase UV, precisely according to instructions.

Calculation

The determined activities of the MAB-amylase mixtures (samples III–VI) are referred to the corresponding activities of the amylase-buffer mixtures (samples I and II) and given as percentage values (samples III and IV are referred to sample I and samples V and VI to sample II).

Results

The influences of the monoclonal antibodies and of the buffer on human salivary and pancreatic α-amylase are illustrated in the following Table:

TABLE 4

| Activity of α-Amylase After Mixing With Various Reagents | | |
|---|---|---|
| | % activity of the | |
| reagent | human salivary α-amylase | human pancreatic α-amylase |
|---|---|---|
| | 100% | 100% |
| D | 111% | 125% |
| E | 113% | 120% |

EXAMPLE 5

Screening system on monoclonal antibodies from culture supernatants of fusions or from ascites or from serum of mice which do not recognise the epitopes of the human α-amylases Nos. I, II, III and V.

The following example of the screening on amylaseactivating MABs does not utilize the activating property of the MABs for the investigation. It is assumed that the amylase has at least 5 epitopes (I–V). The MABs can bind to all these epitopes simultaneously, epitope IV representing the epitope which binds to the activating and cleavage pattern-changing MABs.

Substances polyclonal antiserum against mouse Fc-γ fragments from sheep bovine serum albumin (BSA) (Boehringer Mannheim GmbH, catalogue order No. 238 031)

human salivary α-amylase-horseradish peroxidase conjugate (h-SA=POD) prepared according to M. B. Wilson and P. K. Nakam (see Immunofluorescence and related staining techniques, W. Knapp et al. eds. pub. Elsevier/North Holland Biomedical Press, Amsterdam and New York, 1978, pp. 215–224) from human salivary α-amylase (Sigma, catalogue order No. A 0521) and horseradish peroxidase (Boehringer Mannheim GmbH, catalogue order No. 238 031).

culture supernatant of the hybrid cell clone NCACC 84111301

Fab' fragments of the monoclonal antibodies produced by the hybrid cell clone NCACC 84111301 (MAB against amylase epitope I)

Fab' fragments of the monoclonal antibodies produced by the hybrid cell clone NCACC 84122003 (MAB against amylase epitope II)

Fab' fragments of the monoclonal antibodies produced by the hybrid cell clone NCACC 85022203 (MAB against amylase epitope III)

Fab' fragments of the monoclonal antibodies produced by the hybrid cell clone ECACC 86060601 (MAB against amylase epitope V)

ELISA plates (Nunc, Roskilde, Denmark)

ABTS=2,2-azino-di-[3-ethylbenzthiazoline-6-sulphonate] (Boehringer Mannheim GmbH catalogue order No. 102 946) chemicals of the highest purity from Merck, Darmstadt or Boehringer Mannheim GmbH protective foil for ELISA plates: Plate Sealers catalogue No. M 30 (Dynatech Deutschland GmbH, Denkendorf).

The preparation of the Fab' fragments of the various monoclonal antibodies takes place as follows: ascites (analogously to Example 1/IV)) is first produced of the various hybrid cell clones. From the ascites, via fractionated ammonium sulphate precipitation and via a diethylaminoethylcellulose column (according to A. Johnstone and R. Thorpe in "Immunochemistry in Practice", pub. Blackwell Scientific Publication, Oxford, London, Edinburgh, Boston, Melbourne, 1982, pp. 43–47), the monoclonal antibodies are purified. The cleavage of the antibodies to their Fab' fragments takes place according to A. Nisonoff (Methods Med. Res., 10, 134 et seq./1964).

Reagents

A: sodium carbonate buffer, 50 mM, pH 9.3 with 10 μg./ml. polyclonal antibodies from sheep against Fc-γ-fragments (purified from polyclonal antiserum via ammonium sulphate precipitation and diethylaminoethylcellulose chromatography (A. Johnstone and R. Thorpe in "Immunochemistry in Practice", pub. Blackwell Scientific Publications, Oxford, London, Edinburgh, Boston, Malbourne, 1982, pp. 43–47)

B: PBS/BSA: 100 mM phosphate buffer, 150 mM sodium chloride (pH 7.1) with 1% bovine serum albumin (BSA)

C: reagent B with 200 IU/liter (peroxidase units) h-SA=POD and, in each case, 100 μg./ml. of the four Fab' fragments (of the hybrid cell clones NCACC 84111301, 84122003 and 85022203 and ECACC 86060601); the solution is prepared 1 hour before use.

D: peroxidase substrate solution: 100 mM phosphatecitrate buffer (pH 4.4) with 3.2 mM sodium perborate and 1.9 mM ABTS E: PBS: 100 mM phosphate buffer and 150 mM sodium chloride (pH 7.1).

Carrying out

1. Into each cup of an ELISA plate are pipetted 100 μl. of reagent A. The plates are enclosed with a protective foil and incubated for 18 hours at 4° C.

2. Each cup of the plate is washed three times with at least 250 μl. of reagent E (ambient temperature, in each case for about 5 minutes).

3. Each cup of the plates is incubated with 250 μl. of reagent B (protective foil; ambient temperature, 1 hour).

4. Each cup of the plates is washed as described in 2.

5. Culture supernatant of the various hybrid cell clones or ascites or sera of immunized mice are pipetted undiluted and/or in various dilutions (diluted with reagent B) into various cups of the plates (in each case 100 μl.). The plates are closed and incubated for 2 hours at 37° C. Cups serve as blanks which have only been incubated with reagent B. As negative control, there is used culture supernatant of the hybrid cell clone NCACC 83111301.

6. Each cup of the plates is washed as described in 2.

7. Each cup of the plates is incubated with 100 μl. of reagent C (h-SA=POD+Fab' fragments) (protective foil; 37° C.; 2 hours)

8. Each cup of the plates is washed six times with reagent E (at least 250 μl.; ambient temperature, in each case for about 2 minutes). The cups are sucked dry by means of a water-pump and a fine glass canula.

9. Directly thereafter, into each cup of the plate are introduced 100 μl. of reagent D. The plates are closed with a protective foil and incubated at 37° C. (about 15 to 60 minutes, depending upon the concentration of the MABs to be sought).

Evaluation

The extinctions of the individual cups of the ELISA plates are, after removal of the protective foil, measured in an ELISA reader (Kontron, Switzerland). The extinctions of the blanks (only reagent B) are subtracted from the extinctions of the other cups with MABs.

Cups which are coated with antibodies against the epitope IV of the amylase show clearly higher extinctions than cups which were coated with the culture supernatant of the hybrid cell clone NCACC 84111301. The extinction differences should amount to at least 200 mA.

In this way, there are found, with great probability, all MABs which recognize the epitope IV of the amylase. Surprisingly, these MABs have the property of activating the amylase (i.e. of accelerating the rate of cleavage) and possibly also of changing the cleavage pattern of the substrate.

I claim:

1. Method for determining α-amylase in a sample comprising adding to said sample:
   (i) an α-amylase substrate,
   (ii) a monoclonal antibody which binds to α-amylase in the presence of all of the monoclonal antibodies produced by hybridoma cell lines NCACC 84111301, NCACC 84122003, NCACC 85022203 and ECACC 86060601 and which increases enzymatic activity of α-amylase, and
   (iii) one or more auxiliary enzymes which act on a cleavage product formed by action of α-amylase on said α-amylase substrate, and measuring a cleavage product formed by action of said one or more auxiliary enzymes on the cleavage product formed by the action of α-amylase on its substrate as a measure of α-amylase in the sample.

2. Method according to claim 1 wherein said substrate is a D-maltooligosaccharide with 2 to 10 glucose units.

3. Method according to claim 2 wherein said substrate is a D-maltooligosaccharide with 4 to 8 glucose units.

4. Method according to claim 3 wherein said substrate is maltotetraose and said one or more auxiliary enzyme comprise maltose phosphorylase, β-phosphoglucomutase and glucose-6-phosphate dehydrogenase.

5. Method according to claim 1, wherein said α-amylase substrate is a chromophoric substrate.

6. Method according to claim 5 wherein said chromophoric group is a nitrophenyl radical.

7. Method according to claim 1, wherein said one or more auxiliary enzymes comprises α-glucosidase.

8. Method according to claim 1, wherein said substrate is maltoheptaose and said one or more auxiliary enzymes comprise α-glucosidase, hexokinase and glucose-6-phosphate dehydrogenase.

9. Method according to claim 1, wherein said one or more auxiliary enzymes comprise α-glucosidase and β-glucosidase.

10. Method according to claim 1, wherein said monoclonal antibody which increases activity of α-amylase is produced by hybridoma cell line ECACC 86020601 or hybridoma cell line ECACC 86020602.

11. Method according to claim 1, wherein said substrate contains at least one ethylidene protective group.

12. Method according to claim 1, wherein said α-amylase substrate is a chromophoric substrate and said substrate contains at least one ethylidene protective group.

13. Method for determining one of salivary α-amylase or pancreatic α-amylase in sample, comprising adding to said sample:
   (i) an α-amylase substrate,
   (ii) a monoclonal antibody which binds to α-amylase in the presence of all of the monoclonal antibodies produced by hybridoma cell lines NCACC 84111301, NCACC 84122003, NCACC 85022203 and ECACC 86060601 and which increases enzymatic activity of α-amylase,
   (iii) one or more auxiliary enzymes which act on a cleavage product formed by action of α-amylase on said α-amylase substrate,
   (iv) a monoclonal antibody which inhibits the one of salivary α-amylase or pancreatic α-amylase not being determined and measuring a cleavage product formed by action of said one or more auxiliary enzymes on the cleavage product formed by the action of non-inhibited α-amylase on its substrate as a measure of salivary α-amylase or pancreatic α-amylase in the sample.

14. Method according to claim 13, wherein said α-amylase isoenzyme to be determined is pancreatic α-amylase and said inhibiting monoclonal antibody specifically inhibits salivary α-amylase and is produced by hybridoma cell line NCACC 84122003.

15. Reagent for the determination of α-amylase comprising an α-amylase substrate, one or more auxiliary enzymes which cleave a cleavage product formed by action of α-amylase on its substrate, a system for measuring a cleavage product of said one or more auxiliary enzymes, and at least one monoclonal antibody which increases activity of α-amylase in the presence of all of the monoclonal antibodies produced by hybridoma cell lines NCACC 84111301, NCACC 84122003, NCACC 85022203 and ECACC 86060601.

16. Reagent according to claim 15, wherein said monoclonal antibody which increases α-amylase activity is selected from the group consisting of monoclonal antibodies produced by hybridoma cell lines ECACC 86020601 and ECACC 86020602.

17. Reagent according to claim 15, wherein said α-amylase substrate is a chromophoric substrate.

18. Reagent according to claim 17, wherein said substrate is a D-maltooligosaccharide with 2 to 10 glucose units.

19. Reagent according to claim 18, wherein said reagent comprises maltoheptaose as substrate and α-glucosidase, hexokinase and glucose-6-phosphate dehydrogenase as said one or more auxiliary enzymes.

20. Reagent according to claim 15, wherein said chromophoric group is a nitrophenyl radical.

21. Reagent according to claim 15, wherein said reagent contains α-glucosidase as said one or more auxiliary enzymes.

22. Reagent according to claim 15, wherein said one or more auxiliary enzymes comprise α-glucosidase and β-glucosidase.

23. Reagent according to claim 15, wherein said reagent comprises maltotetraose as substrate and maltose phosphorylase, β-phosphoglucomutase and glucose-6-phosphate dehydrogenase as said one or more auxiliary enzymes.

24. Reagent according to claim 15, wherein said substrate contains at least one ethylidene group.

25. Reagent according to claim 15, wherein said α-amylase substrate is a chromophoric substrate containing at least one ethylidene group.

26. Reagent for determining an α-amylase isoenzyme, comprising:
   (i) an α-amylase substrate, (ii) one or more auxiliary enzymes which cleave a cleavage product formed by action of α-amylase on its substrate, (iii) a system for measuring a cleavage product of said one or more auxiliary enzymes, (iv) at least one monoclonal antibody which increases activity of α-amylase in the presence of all of the monoclonal antibodies produced by hybridoma cell lines NCACC 84111301, NCACC 84122003, NCACC 85022203 and ECACC 8606061, (v) and an additional monoclonal antibody which inhibits activity of the isoenzyme not being determined.

27. Reagent according to claim 26 wherein said additional monoclonal antibody is a monoclonal antibody against salivary α-amylase produced by hybridoma cell line NCACC 84122003.

28. Reagent according to claim 27 further comprising monoclonal antibody against salivary α-amylase produced by hybridoma cell line NCACC 84111301.

29. Reagent according to claim 27, wherein said reagent further comprises at least one of the monoclonal antibodies against salivary α-amylase formed by hybridoma cell lines NCACC 85022203 and ECACC 86060601.

30. Kit for determination of α-amylase comprising separate samples, each of which is in a separate container, of
   (i) an α-amylase substrate,
   (ii) one or more auxiliary enzymes which cleave a cleavage product formed by action of α-amylase on its substrate,
   (iii) a system for measuring a cleavage product formed by action of said one or more auxiliary enzymes in the cleavage product formed by action of α-amylase on its substrate, and
   (iv) at least one monoclonal antibody which increases activity of α-amylase in the presence of all of the monoclonal antibodies produced by hybridoma cell lines NCACC 84111301, NCACC 84122003, NCACC 85022003 and ECACC 86060601.

31. Kit for determination of an α-amylase isoenzyme comprising separate portions of each of
   (i) an α-amylase substrate,
   (ii) one or more auxiliary enzymes which cleave a cleavage product formed by action of α-amylase on its substrate,
   (iii) a system for measuring a cleavage product formed by action of said one or more auxiliary enzymes in the cleavage product formed by action of α-amylase on its substrate,
   (iv) at least one monoclonal antibody which increases activity of α-amylase in the presence of all of the monoclonal antibodies produced by hybridoma cell lines NCACC 84111301, NCACC 84122003, NCACC 85022003 and ECACC 86060601, and
   (v) a monoclonal antibody which inhibits activity of the α-amylase isoenzymes not being determined.

* * * * *

UNITED STATES PATENT AND TRADEMARK OFFICE
CERTIFICATE OF CORRECTION

PATENT NO. : 4,945,043
DATED : July 31, 1990
INVENTOR(S) : Martin Gerber

It is certified that error appears in the above-identified patent and that said Letters Patent is hereby corrected as shown below:

Column 16, line 7: change "85022003" to -- 85022203 --.

Column 16, line 22: change "85022003" to -- 85022203 --.

Signed and Sealed this

Ninth Day of June, 1992

Attest:

DOUGLAS B. COMER

*Attesting Officer*

*Acting Commissioner of Patents and Trademarks*